(12) United States Patent
Chang et al.

(10) Patent No.: US 12,733,956 B2
(45) Date of Patent: Sep. 15, 2026

(54) METHODS AND SYSTEMS FOR ABRASIVE TIP FLUID DELIVERY FOR MICRODERMABRASION

(71) Applicants: Franklin J. Chang, Pasadena, CA (US); Henry Ping Chang, Pasadena, CA (US)

(72) Inventors: Franklin J. Chang, Pasadena, CA (US); Henry Ping Chang, Pasadena, CA (US)

( * ) Notice: Subject to any disclaimer, the term of this patent is extended or adjusted under 35 U.S.C. 154(b) by 0 days.

(21) Appl. No.: 19/071,679

(22) Filed: Mar. 5, 2025

(65) Prior Publication Data

US 2026/0263114 A1 Sep. 10, 2026

(51) Int. Cl.

| | |
|---|---|
| ***A61M 37/00*** | (2006.01) |
| ***A61B 17/54*** | (2006.01) |
| *A61B 17/00* | (2006.01) |
| *A61B 17/32* | (2006.01) |

(52) U.S. Cl.

CPC ............. *A61B 17/54* (2013.01); *A61M 37/00* (2013.01); *A61B 2017/00747* (2013.01); *A61B 2017/320004* (2013.01); *A61B 2217/005* (2013.01); *A61M 2037/0007* (2013.01)

(58) Field of Classification Search

CPC .......... A61B 17/54; A61B 2017/00747; A61B 2017/00761; A61B 2017/320004; A61B 2218/001; A61M 2037/0007

See application file for complete search history.

(56) References Cited

U.S. PATENT DOCUMENTS

| | | | | |
|---|---|---|---|---|
| 9,044,582 | B2 * | 6/2015 | Chang | A61M 37/00 |
| 9,138,257 | B2 | 9/2015 | Cohen et al. | |
| 9,486,615 | B2 | 11/2016 | Ignon | |
| 10,098,653 | B2 | 10/2018 | Presser et al. | |
| 10,130,390 | B1 | 11/2018 | Hart et al. | |
| 10,456,321 | B2 | 10/2019 | Shadduck | |
| 10,729,287 | B2 | 8/2020 | Powell et al. | |
| 11,744,999 | B2 | 9/2023 | Ignon | |
| 11,806,495 | B2 | 11/2023 | Ignon | |
| 11,925,780 | B2 | 3/2024 | Ignon | |
| 12,005,217 | B2 * | 6/2024 | Ignon | A61B 17/54 |
| 2018/0353101 | A1 * | 12/2018 | Ouwerkerk | A61B 5/0531 |
| 2021/0145478 | A1 | 5/2021 | Boone | |

* cited by examiner

*Primary Examiner* — Deanna K Hall
(74) *Attorney, Agent, or Firm* — Sam Pierce

(57) ABSTRACT

An embodiment of the present invention is a motor-driven tip with molded grooves and shapes connected to a spindle shaft, enabling unparalleled depth during each pass and reaching multiple layers of the skin. Each tip incorporates one or more fluid apertures strategically positioned to facilitate both vacuum suction and fluid outlet functionalities. Each tip is a plastic tips with abrasives. First, the adhesive is electrostatically sprayed onto the surface. Then, the sand is electrostatically sprayed onto the surface. Another embodiment is a serum bottle attachment. This embodiment allows for swift, customized, and versatile application of various skincare fluids. The handpiece facilitates the seamless connection and removal of serum bottles.

13 Claims, 16 Drawing Sheets

20
30
40
50
82
70
2
100
10
1
60
102
104
100
90
102

METHODS AND SYSTEMS FOR ABRASIVE TIP FLUID DELIVERY FOR MICRODERMABRASION

BACKGROUND

U.S. Pat. No. 9,186,490 to the present inventor described a skin treatment device including a handle and a tip, having a skin applying surface, detachably coupled to the handle. A fluid delivery structure is formed at skin applying surface and has an aperture and a vacuum entry port. A fluid detouring path is defined between the aperture and the vacuum entry port for prolonging a traveling path of fluid from the aperture and the vacuum entry port. An abrading structure, an electrode structure, and a micro-needling structure are selectively provided at the skin applying surface with the fluid delivery structure to provide multiple functions of the tip.

U.S. Pat. No. 9,044,582 to the present inventor disclosed an apparatus for transdermal fluid delivery including a handle and a tip, having a skin applying surface, being driven to move by a driving unit. A fluid delivery structure has an aperture formed at the skin applying surface and a vacuum entry port. An abrading structure, an electrode structure, and a micro-needling structure are selectively provided at the skin applying surface with the fluid delivery structure to provide multiple functions of the tip. A flow of fluid is delivered onto the skin applying surface through the fluid delivery structure to interact with the abrading elements and the electrodes before the fluid is returned and collected, so that three different skin treatments of abrasive peeling, electrical stimulation, and liquid infusion are achieved in one single structure for improving a skin structure.

There remains however a need for improved fluid delivery to ensure the skin receives the full benefit of the infused skincare fluids.

SUMMARY OF INVENTION

Therefore, an embodiment of the present invention is an abrasive motor-driven tip with molded grooves and shapes connected to a spindle shaft, enabling unparalleled depth during each pass and reaching multiple layers of the skin. Each tip incorporates one or more fluid apertures strategically positioned to facilitate both vacuum suction and fluid outlet functionalities.

According to an aspect of the present invention, there is provided tip for a microdermabrasion device, comprising: one or more fluid apertures positioned to facilitate both vacuum suction and fluid outlet functionalities; and one or more grooves, wherein: the tips are crafted from a plastic material; and the tips have an abrasive coating.

The abrasive tip has an adhesive, such as epoxy resin, and an abrasive such as emery sand.

DETAILED DESCRIPTION

Treatment of the skin can be done transdermally to penetrate fluid deeper into the skin by means of simultaneous 1) abrasive peeling 2) electrical stimulation 3) liquid infusion to improve the skin structure affecting multiple layers of the skin, such as, epidermis, dermis, and hypodermis.

An embodiment of the present invention is a microdermabrasion device featuring:

1. Motor-driven tips with variable rotational speeds (10 to 300 RPM) for controlled exfoliation and fluid infusion.
2. Advanced abrasive coatings applied through an electrostatic process and cured for durability.
3. Integrated fluid delivery and vacuum system within a rotating tip, with a stationary cap creating a vacuum space to facilitate fluid travel.
4. Interchangeable tips offering various treatments (abrasive peeling, electrical stimulation, fluid infusion).
5. Ergonomic handle design and quick-connect serum bottle attachment for enhanced user comfort and convenience.

Figure 1:
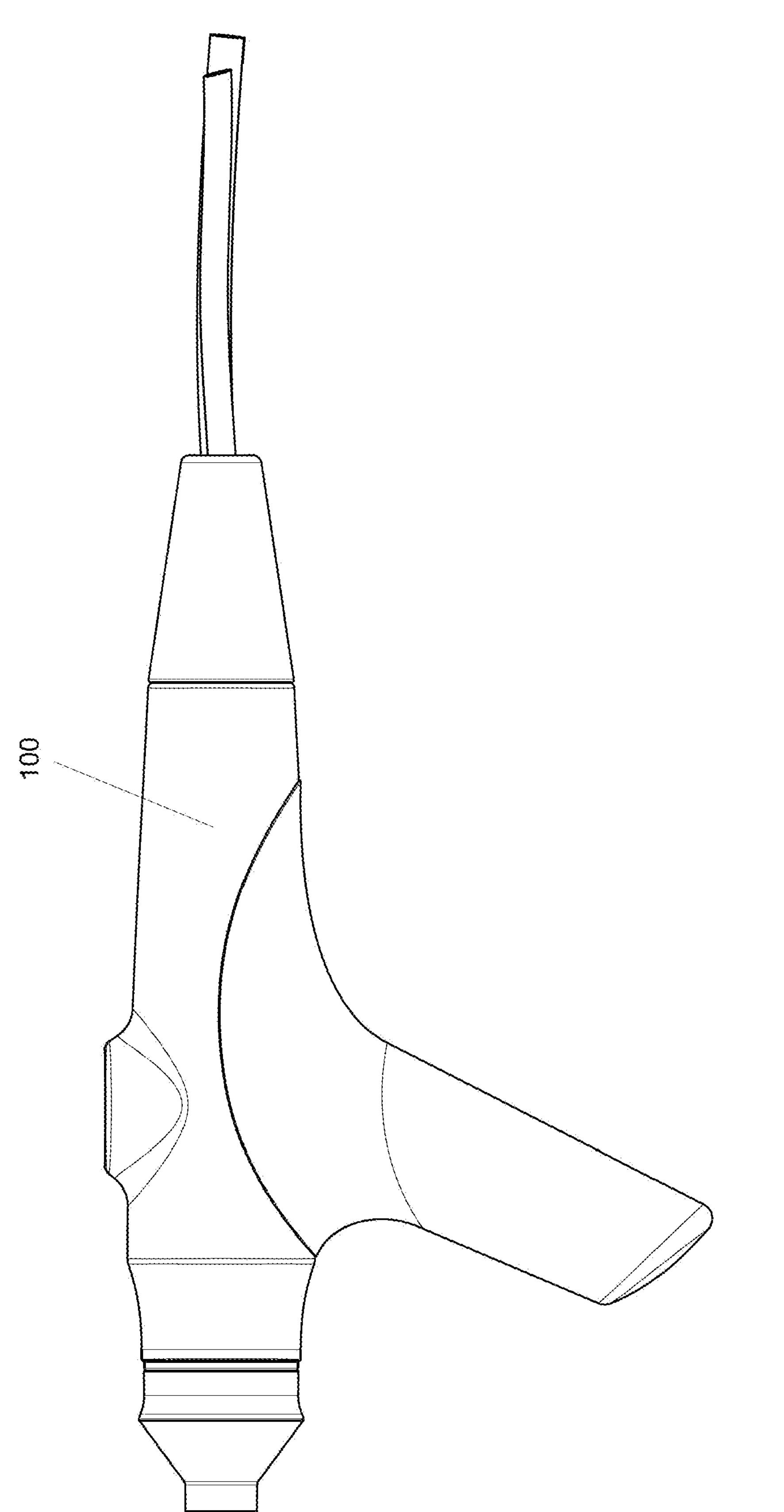
FIG. 1—Device
Figure 2:
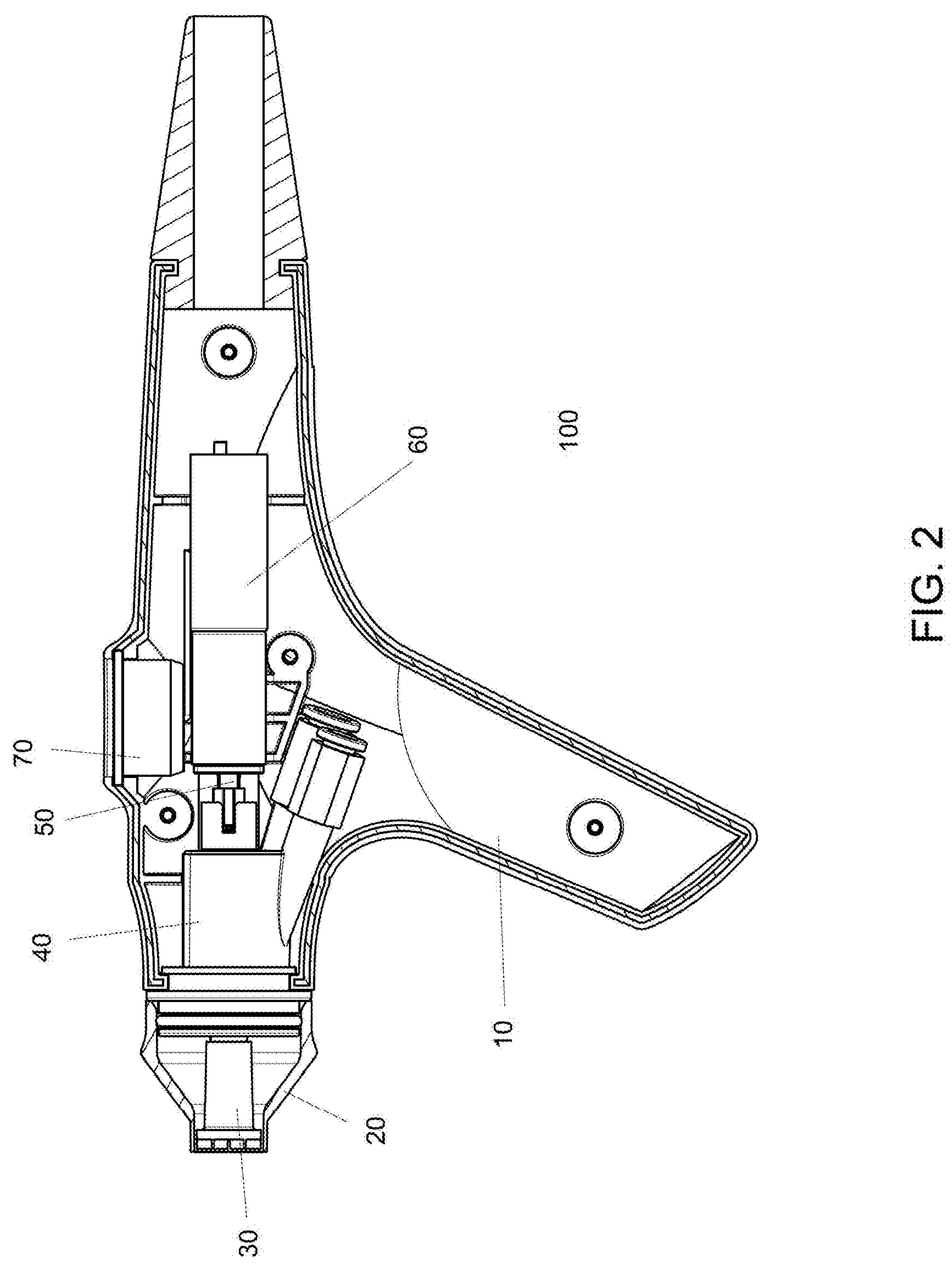
FIG. 2—cross section view of the device
Figure 3:
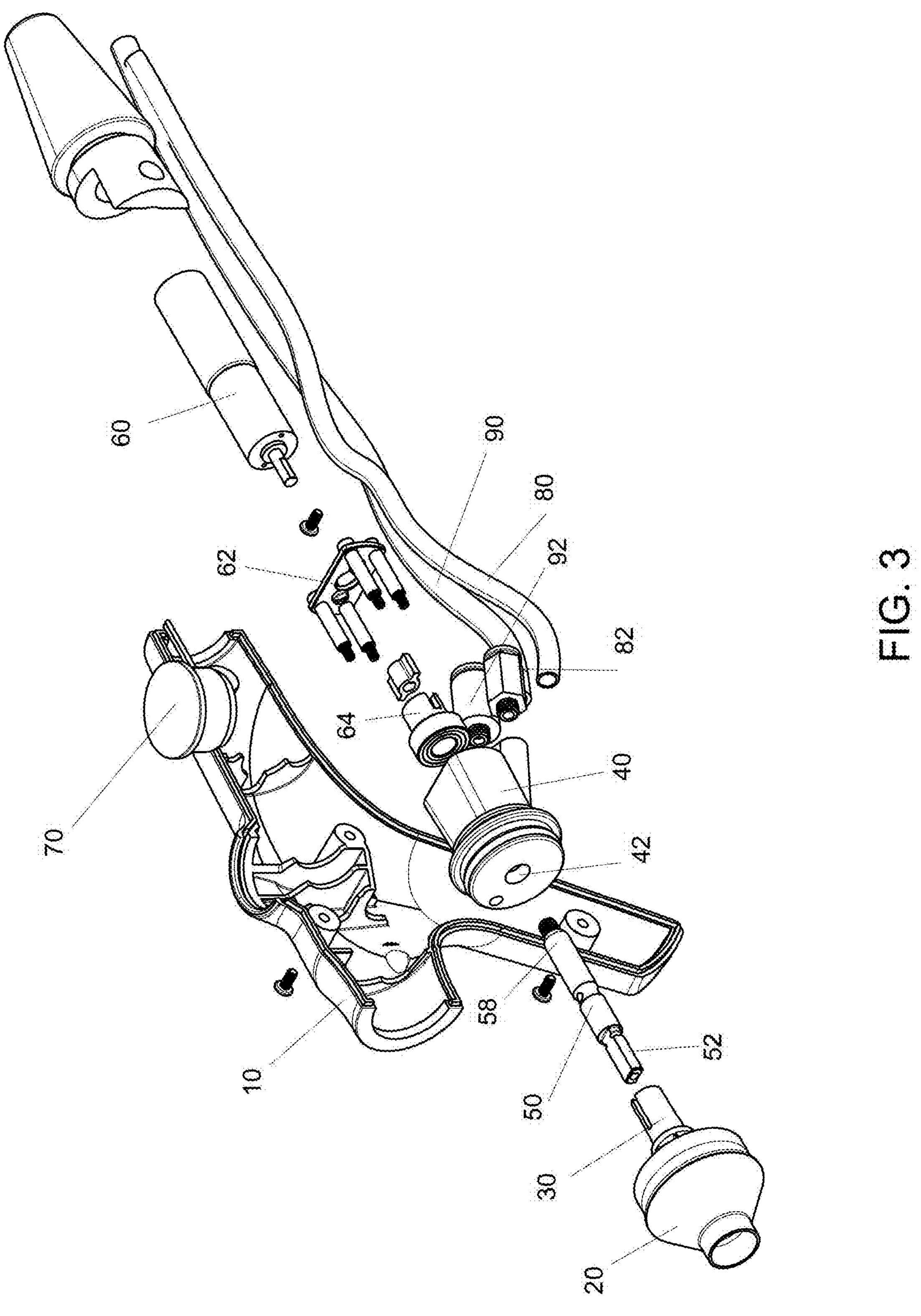
FIG. 3—exploded view of the device
Figure 4:
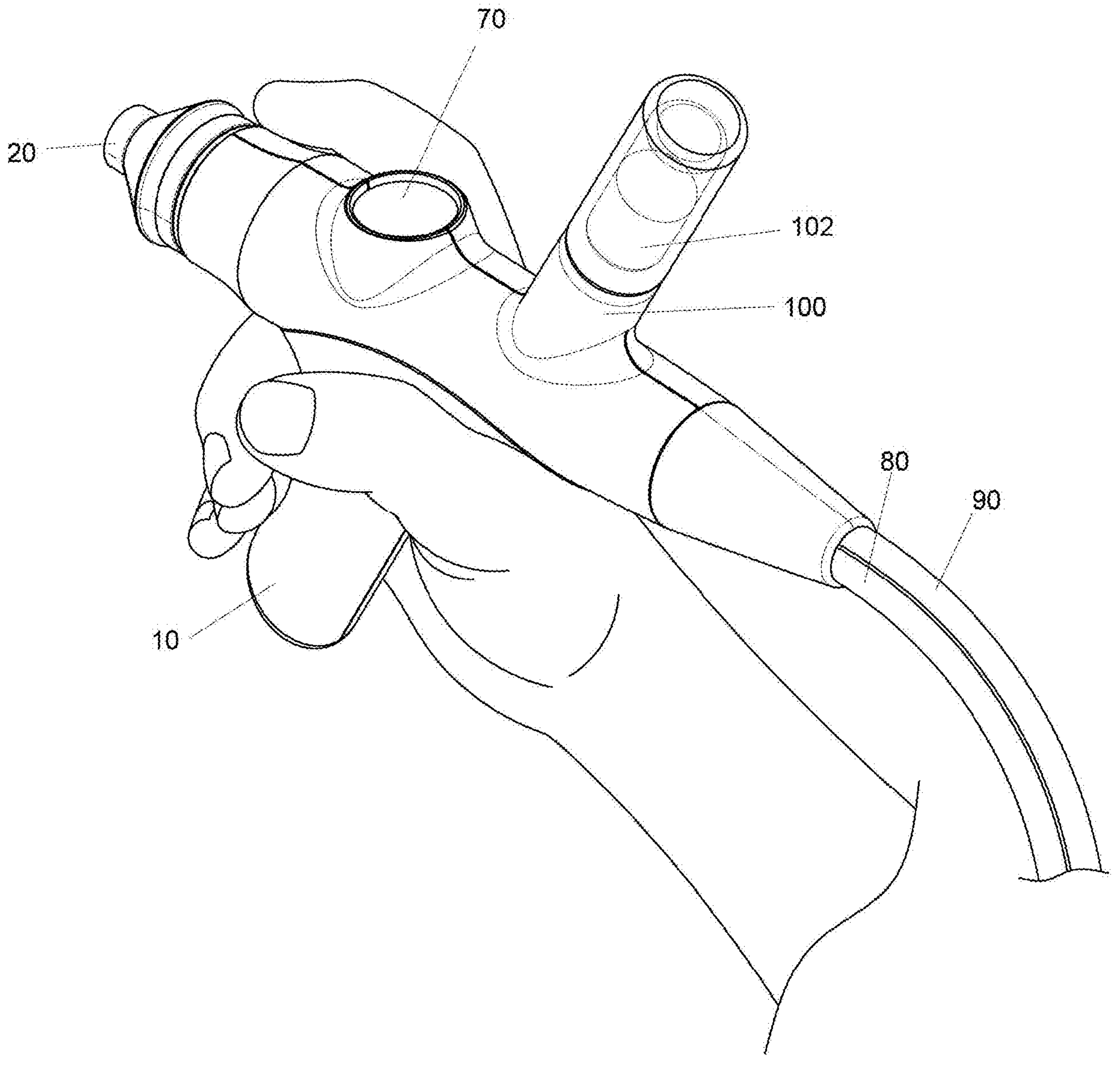
FIG. 4-6—An embodiment with serum attachment
Figure 5:
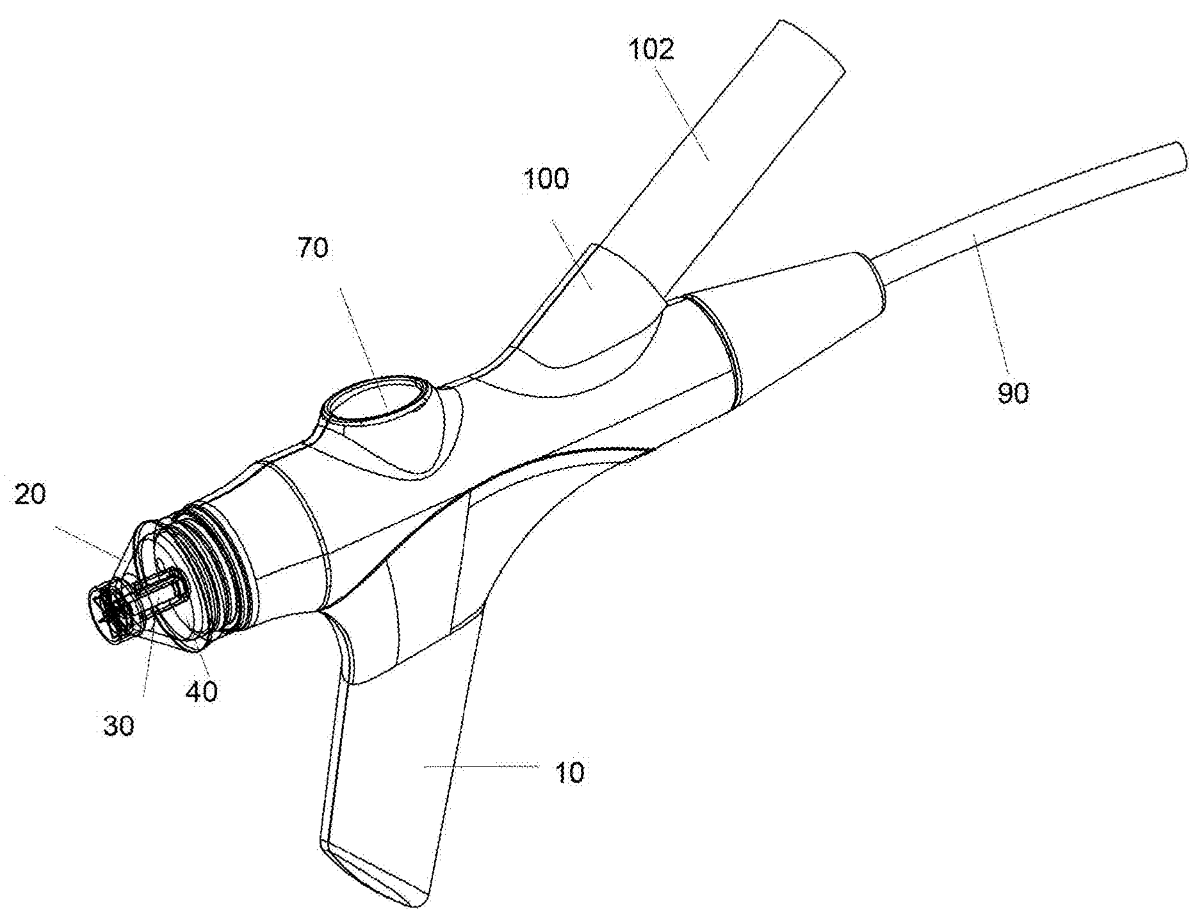
Figure 6:
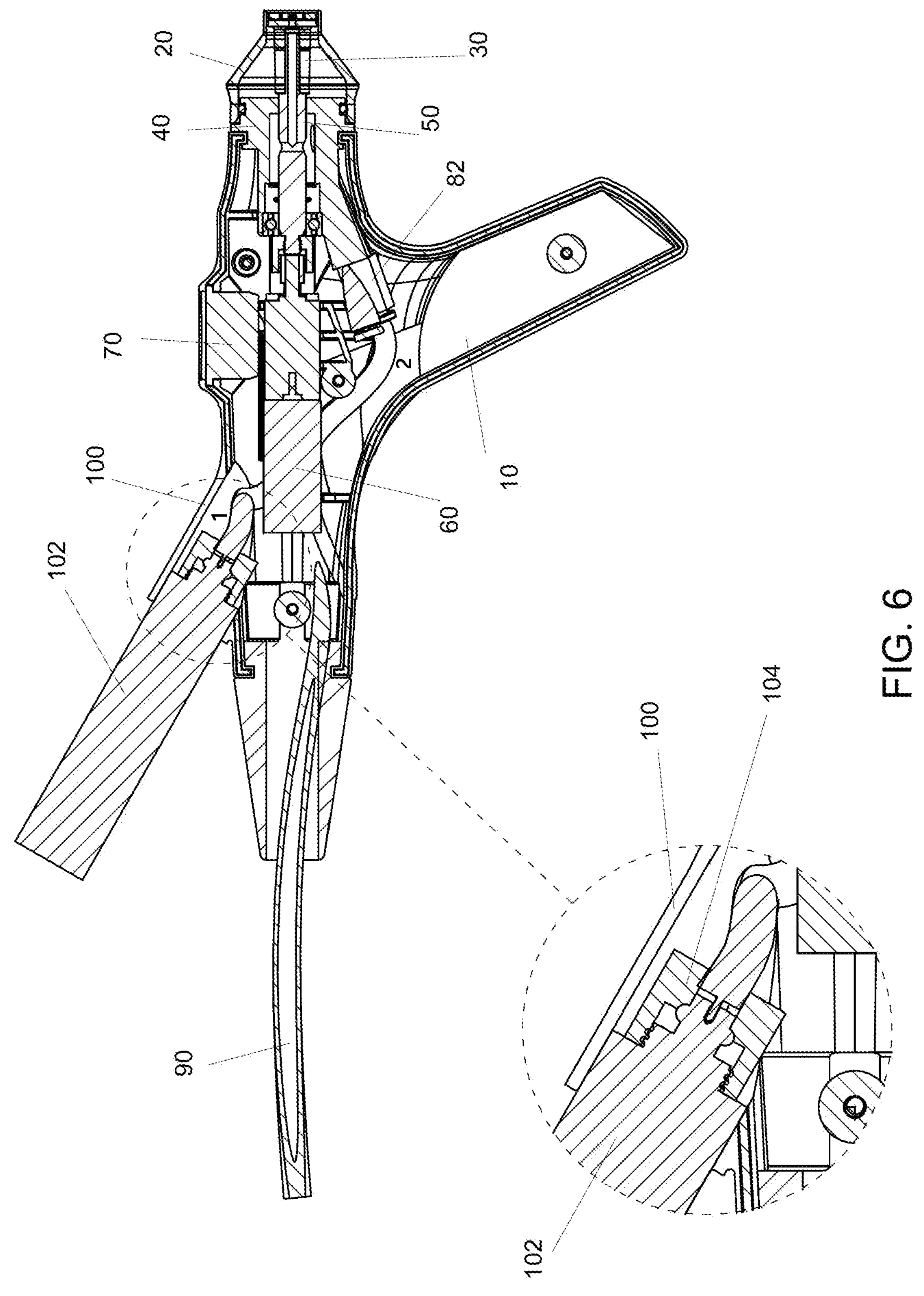
Figure 7:
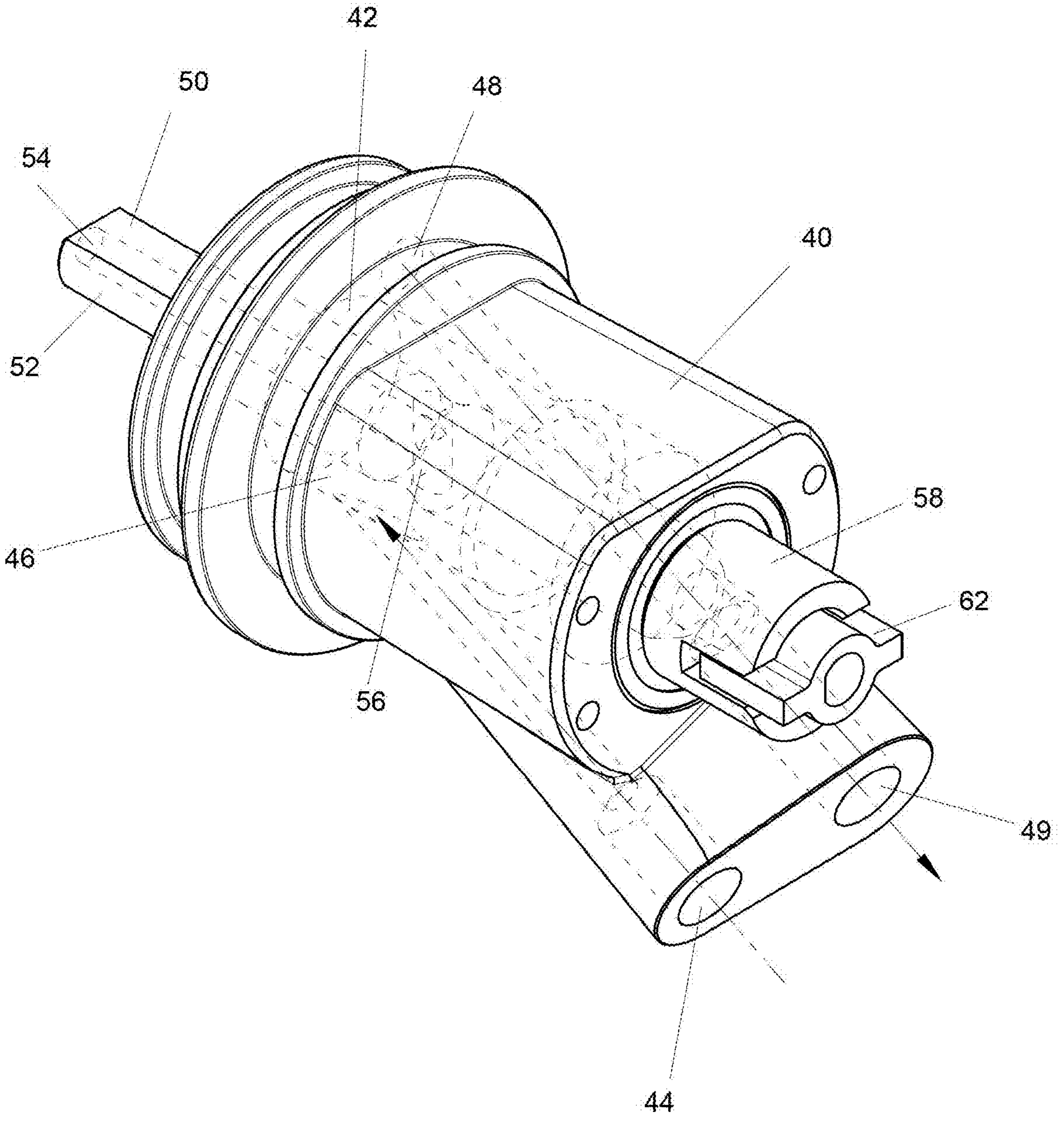
FIG. 7—Detailed view of the core of the device
Figure 8:
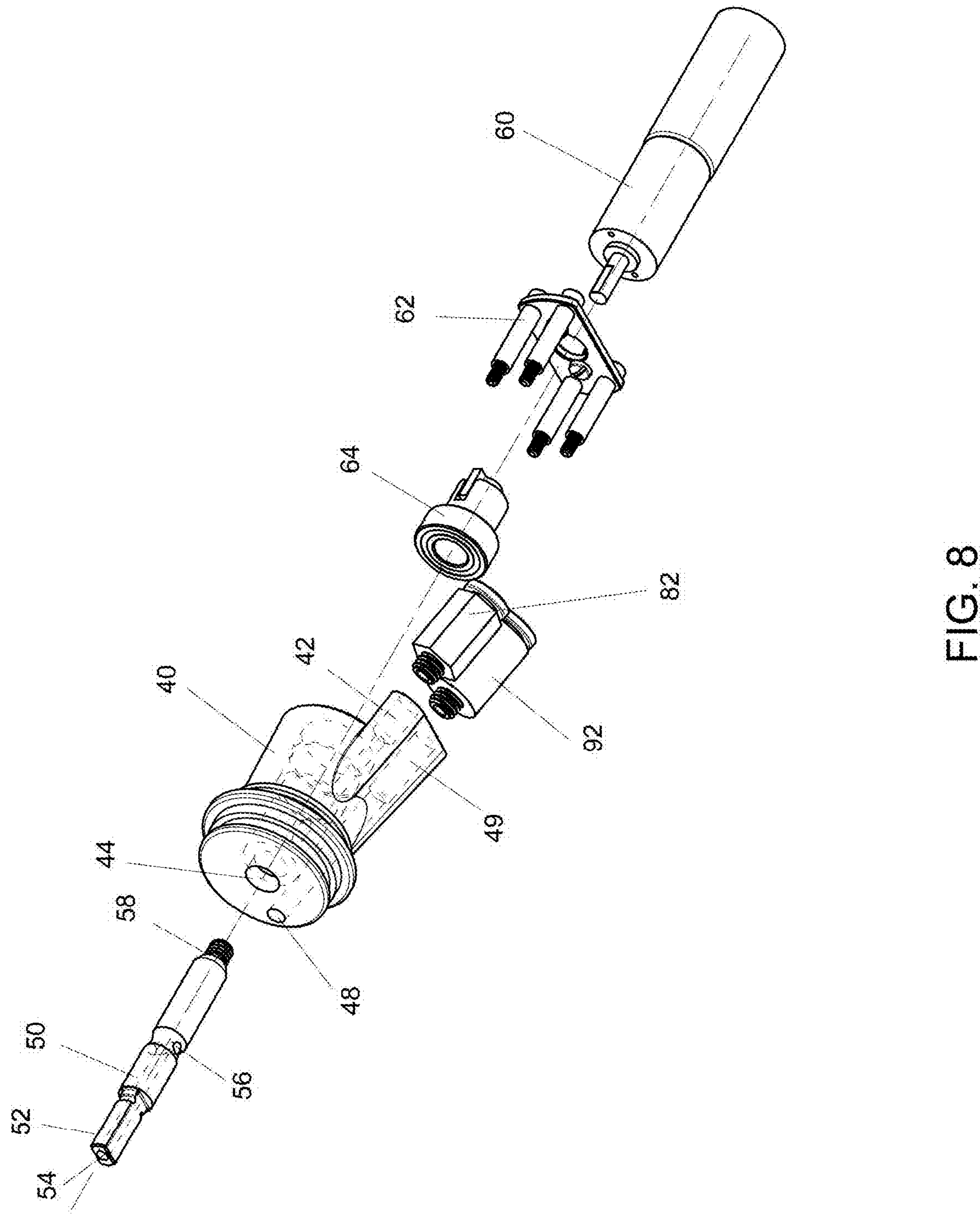
FIG. 8—exploded view of the core with the shaft, motor and tube couplings
Figure 9:
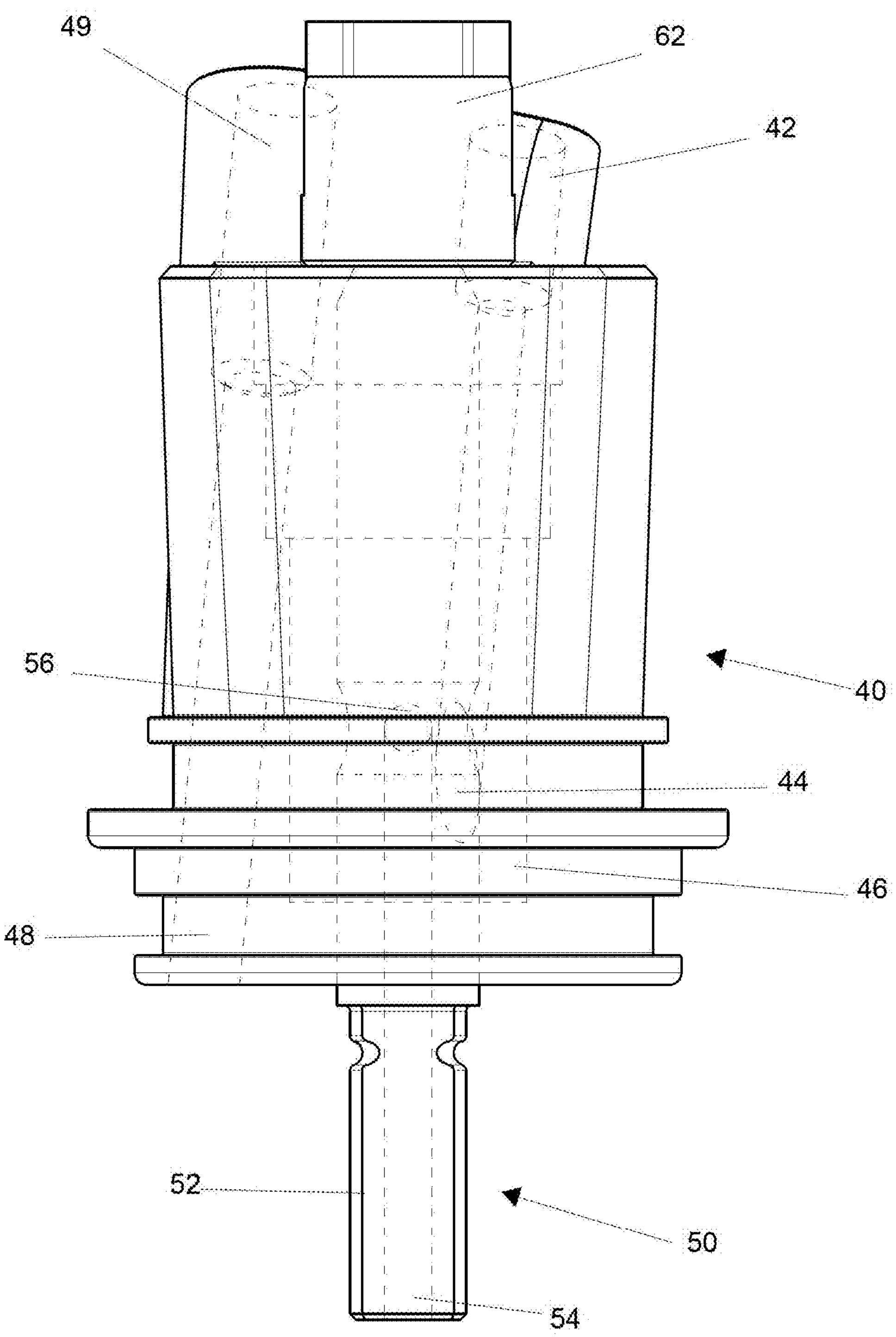
FIG. 9—Top view of core with shaft
Figure 10:
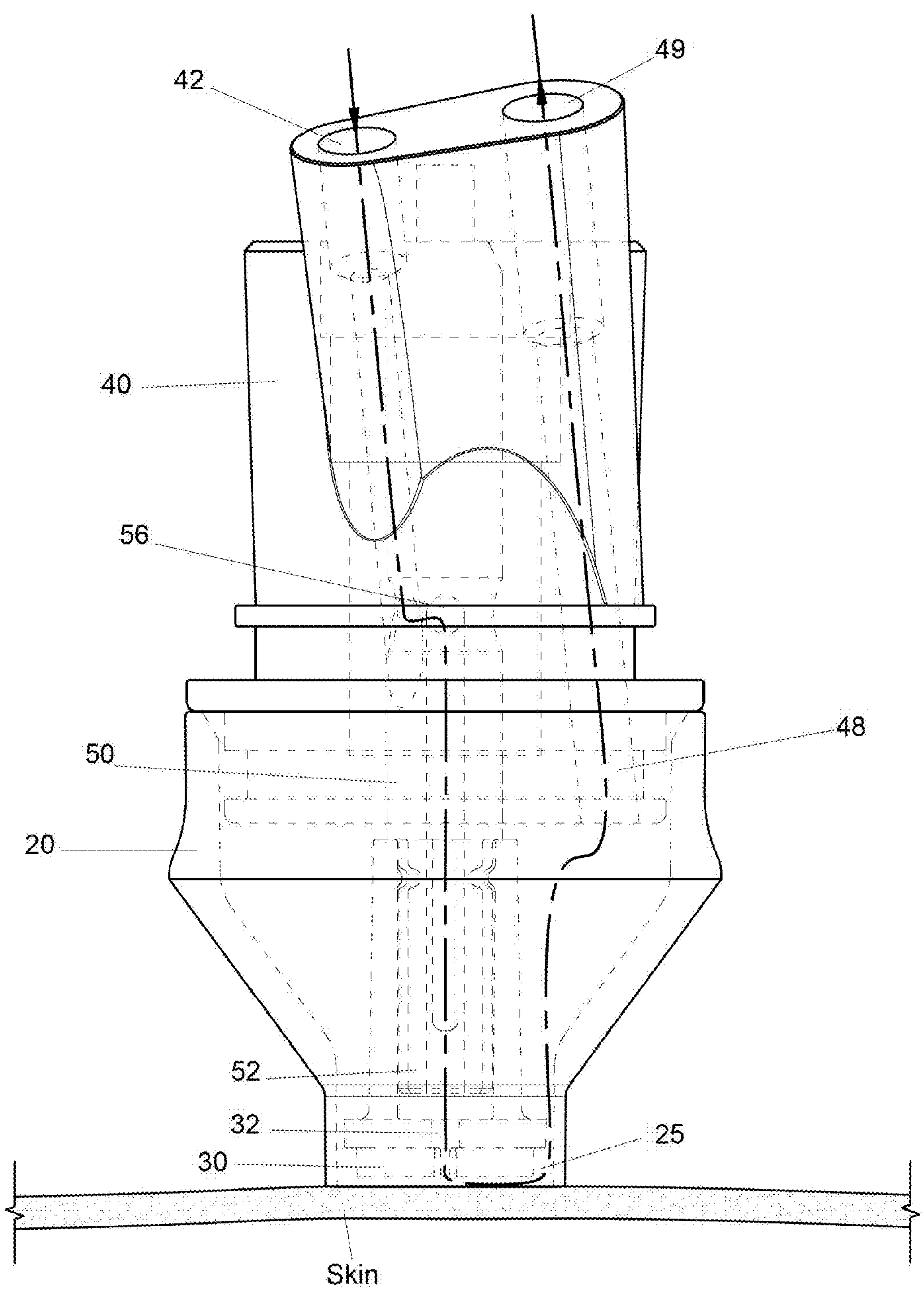
FIG. 10—Fluid flow showing fluid coming from inlet 42, entering the shaft through aperture 56 and coming out of the hole 52, after contacting the skin, the fluid pass through the gap 25 and is sucked through the suction port 48, and sent outside through outlet port 49 and further to tube 90.
Figure 11:
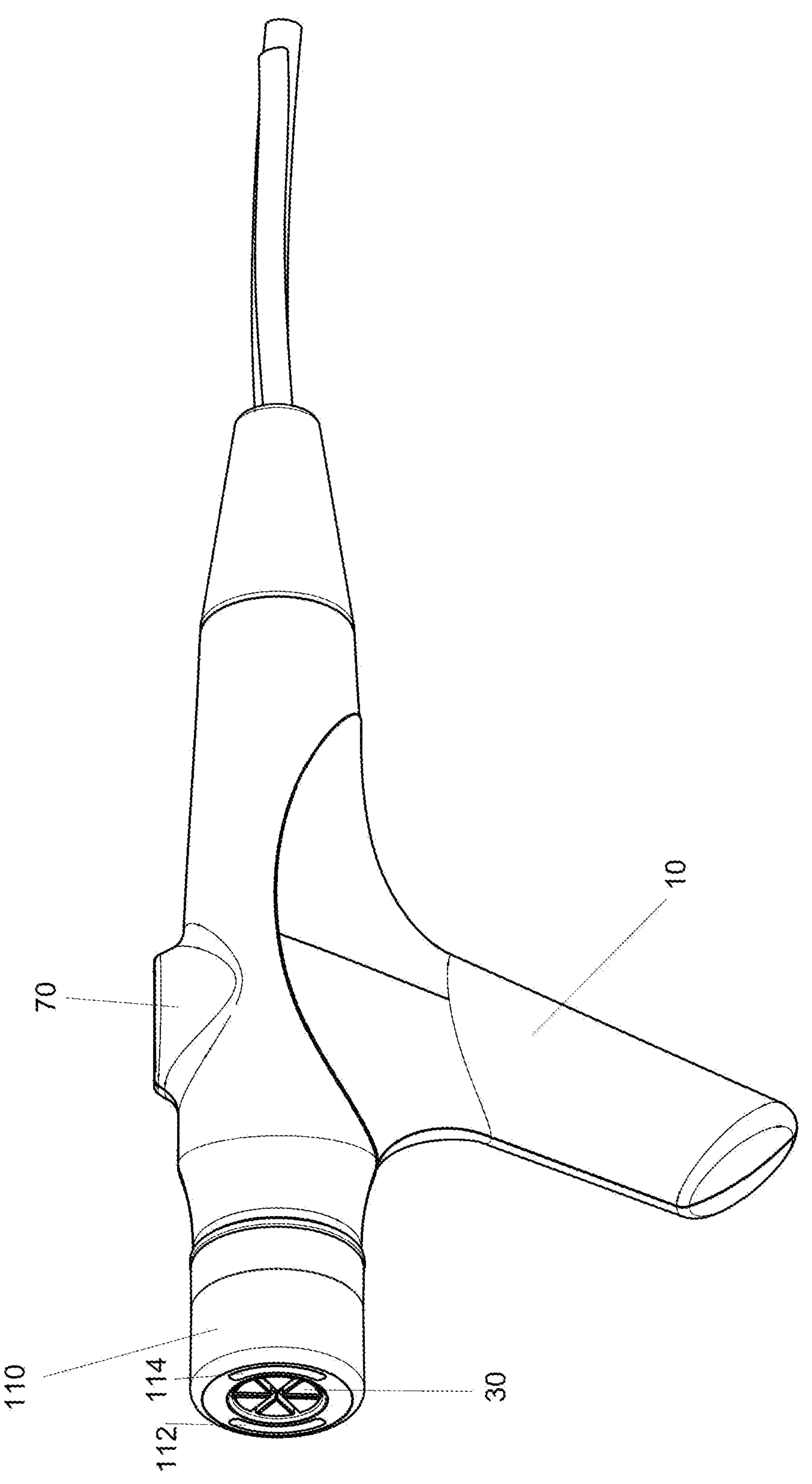
FIG. 11—an embodiment with the device comprising electrodes 112, 114 on the tip cover FIG. 12—exploded view of the tip cover with tip and core for the embodiment of FIG. 11
Figure 12:
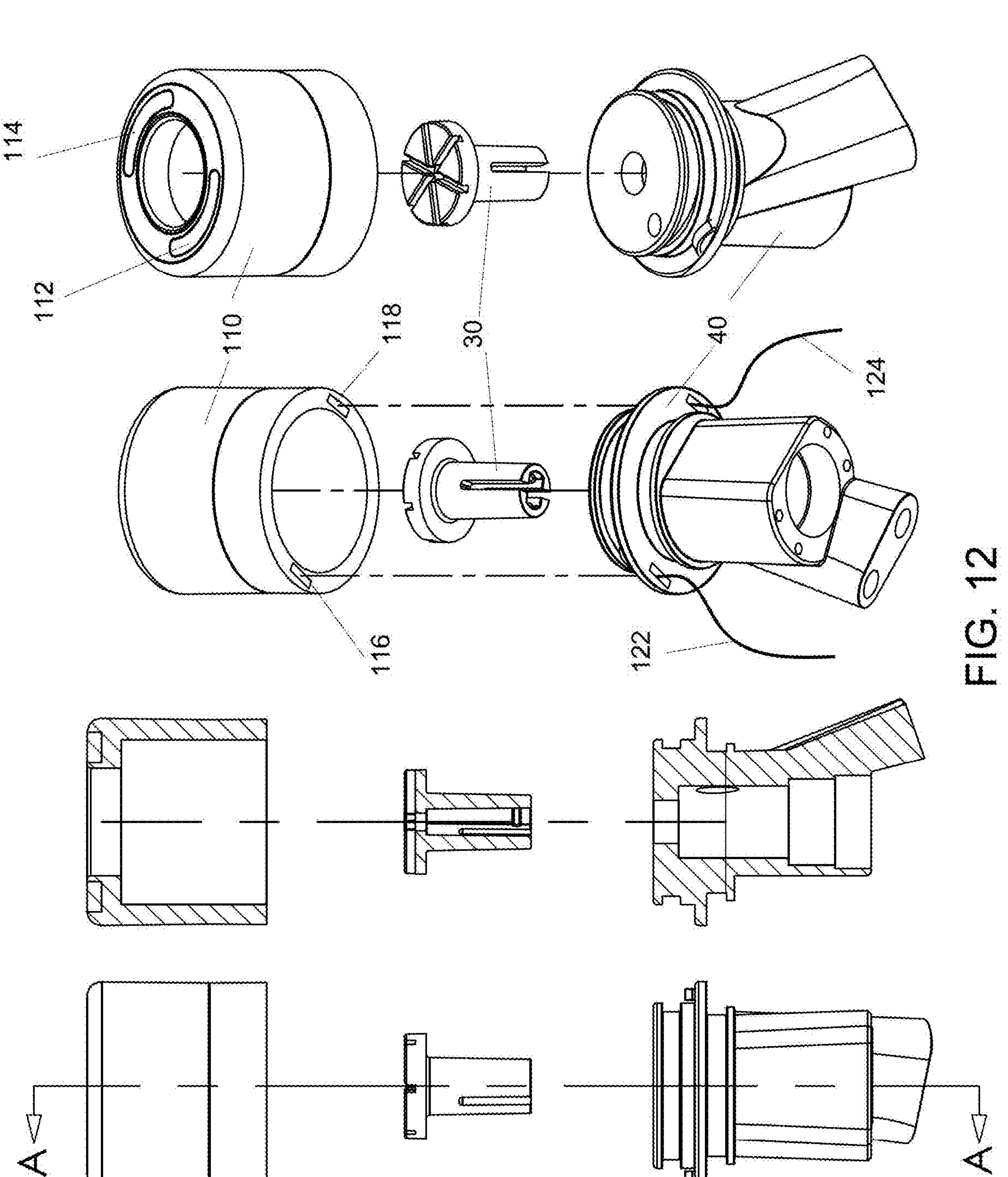
Figure 13A:
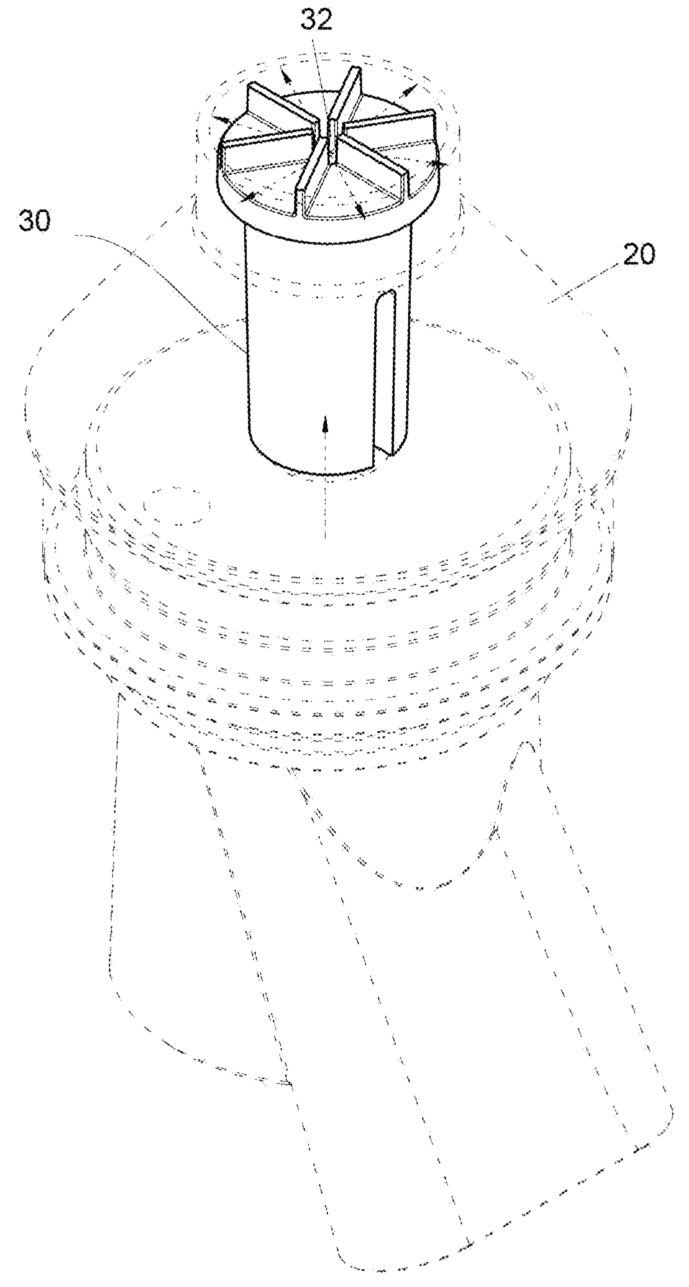
FIG. 13A—working of tip
Figure 13B:
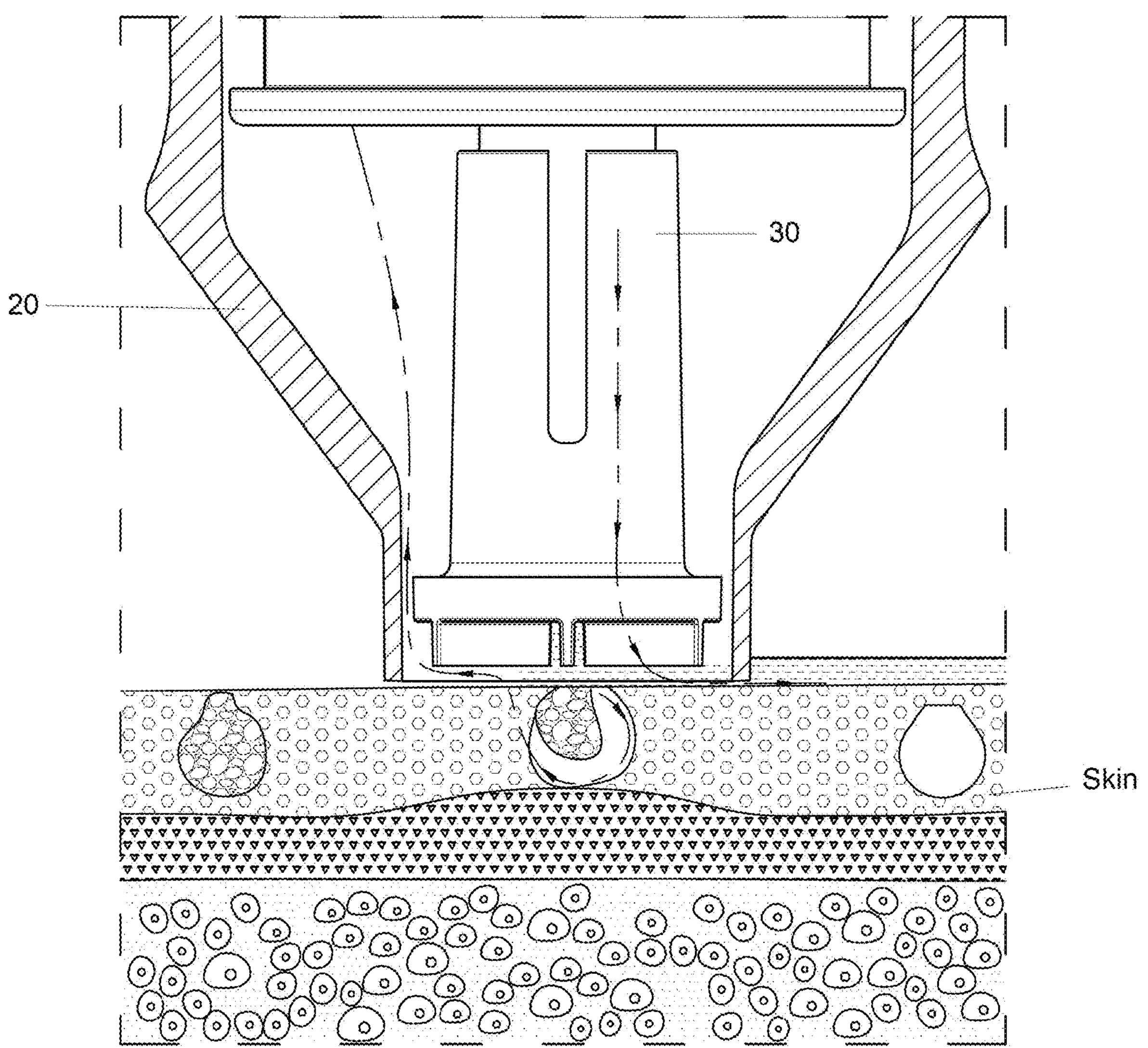
FIG. 13B—cross section of working of tip
Figure 14A:
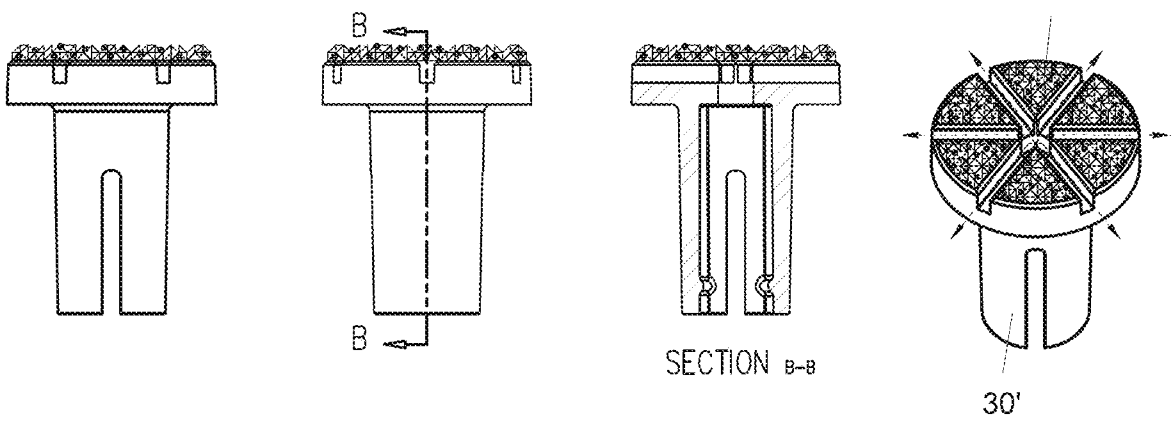
FIG. 14A—working of the abrasive tip
Figure 14B:
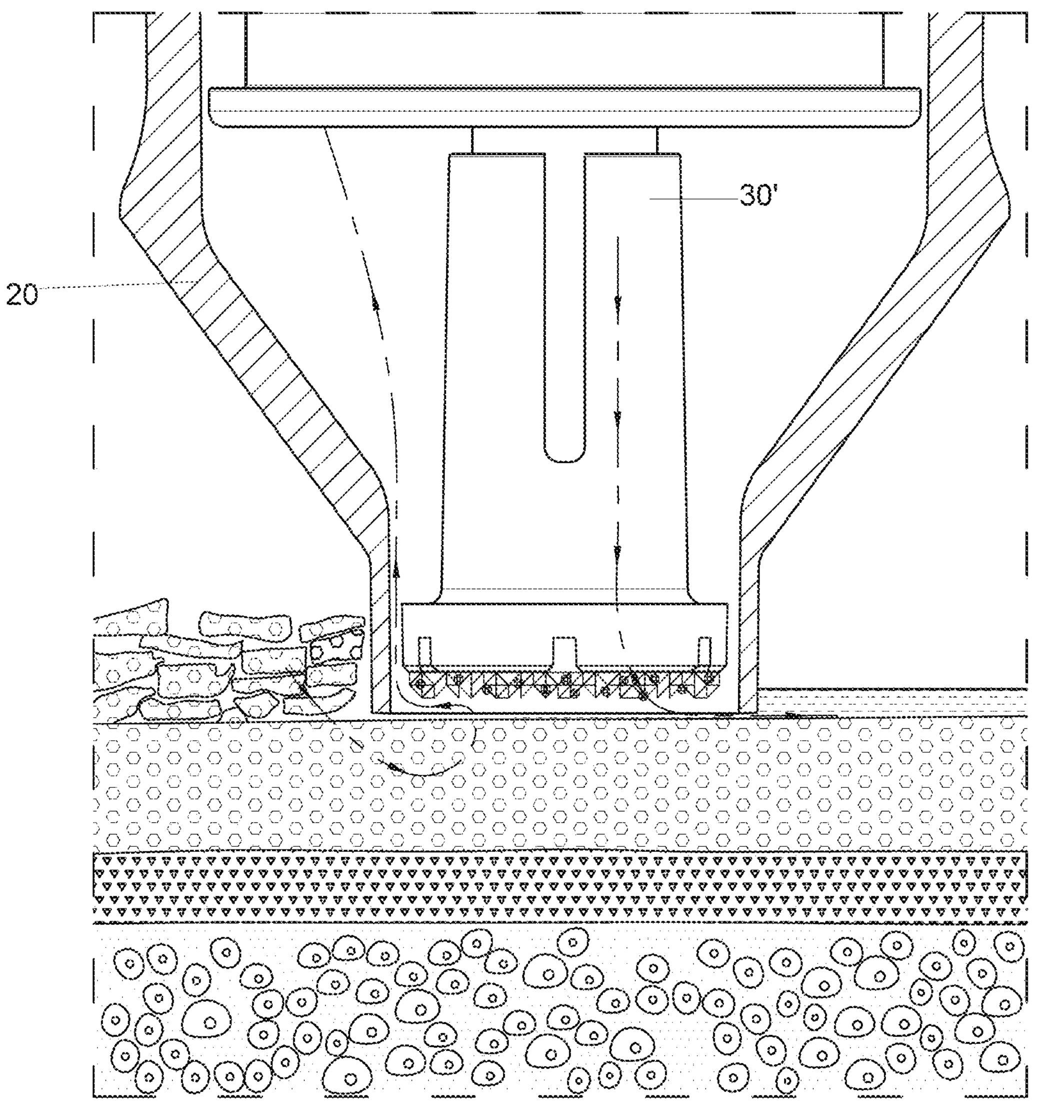
FIG. 14B—cross section of working of the abrasive tip

The following features are indicated in FIG. 1-14:

10—Housing

20—Tip cover

25—Gap between the tip and internal walls of the tip cover

30—Tip

32—tip opening

30'—Abrasive Tip

32—Opening for abrasive tip

40—core

42—main hole for the shaft

44—core inlet

46—cavity for fluid connection between core and the shaft 50

48—suction hole

49—core outlet

50—shaft

52—proximal end of the shaft

54—distal end of the shaft

56—aperture for fluid outlet through shaft

56—aperture for fluid connection between core and the shaft 50

60—motor

62—mounting part of the motor

64—coupling for motor and shaft

70—button/switch

80—inlet tube

82—first tube coupling attached to the core inlet

90—outlet tube

92—second tube coupling attached to the core outlet

100—attachment part for serum

102—serum cartridge
104—coupling part for serum cartridge
110—embodiment for the tip cover
112, 114—electrodes for electrical impulses on the skin
116, 118—connections for electrodes to receives electrical current
122, 124—wiring provided through the core 40 for electrical connections 116,118
1—first tubing segment
2—second tubing segment The devices and systems described herein allow for the simultaneous deep penetration of fluid through the skin by applying an electric current and an abrasive media in the working end of the device to increase skin's permeability. According to alternate embodiments, techniques known as electroporation, ultrasound, and other electrical induced therapies, etc., which use electric currents to go deeper past the stratum corneum to stimulate cells underneath the skin may be employed in the device. The combination of the electrical induced therapies and microdermabrasion create aqueous pathways to increase the permeability of the drugs and/or fluids which are delivered from a supply and return reservoir by a vacuum system within the device. A pressure mechanism may also be employed as part of the device.

A device for treating a skin surface of a patient comprising a handle having a tip at the proximal end of the handle is intended to be used with embodiments of the present invention. The tip has one or more electrodes and an abrading end portion which has an abrasive media and one or more apertures for fluid delivery. The device may also have a vacuum and a vacuum entry port located on the tip at the proximal end of the handle, where the vacuum entry port has one or more apertures for evacuating fluid and debris from the surface of the skin. According to another embodiment, the electrodes, abrading end portion and fluid delivery apertures are positioned on the tip of the handle, where each one individually may be on a removable tip or end structure. When the device has a plurality of removable structures, the end structures may also be separately removable and interchangeable.

The abrasive tip has an adhesive, such as epoxy resin, and an abrasive such as emery sand.

For the plastic tips with abrasives, this is the process. First, the adhesive is electrostatically sprayed onto the surface. Then, the sand is electrostatically sprayed onto the surface. The final step is to bake at a temperature of 80° C. for 2 hours.

The tip integrates multiple functions within a single unit, including a substantially smooth to abrasive coating for superior exfoliation, strategically designed grooves or shapes facilitating vacuum-driven infusion of skincare fluids while efficiently removing abraded skin debris.

The device is anchored by a motor-driven tip connected to a spindle shaft, enabling unparalleled depth during each pass, reaching multiple layers of the skin. Unlike traditional stationary tips, our motor-driven approach exfoliates and infuses at depths ranging from 10-300 revolutions per minute, ensuring consistent and controlled skin treatment.

The tips are crafted from a plastic material, featuring an abrasive coating, preferably composed of aluminum oxide or a mixture of metals, meticulously attached through an adhesive or polymer process. Importantly, each tip incorporates one or more fluid apertures strategically positioned to facilitate both vacuum suction and fluid outlet functionalities. These apertures are instrumental in optimal fluid delivery, ensuring that the skin receives the full benefit of the infused skincare fluids.

Moreover, the tips are engineered with molded grooves and shapes, creating pathways that enhance fluid penetration while allowing efficient debris removal through vacuum suction. Unlike existing devices with flat tips or metal electroplated options, our design eliminates barriers to fluid flow, providing a more effective and consistent skincare experience.

One of the features of a device using the tips of the present invention is its ability to spot treat specific skin areas, a task challenging for traditional stationary tips. This pinpoint accuracy, coupled with the motor-driven action, enables precise treatments and reduces the risk of skin irritation caused by excessive pressure or scratching motions.

Additionally, the device excels in body treatments. The thicker skin on the body, often presenting a formidable barrier, is efficiently exfoliated and infused due to the device's motor-driven power. This capability significantly expands the device's utility beyond facial treatments.

The ergonomic and custom-designed handpiece, coupled with the motor-driven tip, minimizes operator fatigue, ensuring a comfortable and efficient treatment experience. Operators benefit from reduced hand strain, allowing for extended use without compromising the quality of treatment. The motor-driven tip not only enhances effectiveness but also expedites the treatment process, offering faster results while maintaining superior exfoliation and infusion depths.

Additionally, the invention introduces advanced embodiments such as an electrical function detachable cap for stimulating multiple skin layers.

The motor-driven handpiece features an opening molded to mate with a serum bottle. The opening comprises a male connection equipped with threads or a puncturing tube. The serum bottle is fitted with a cap or foil cap, threaded or connected to the male tube upon insertion. The male tube punctures or threads onto the serum bottle, forming a secure seal and allowing fluid to flow through a vacuum tube inside the handpiece.

The serum flows through the spindle shaft and the attached multifunctional tip onto the skin applying surface. This innovative attachment enables the application of various skincare fluids, including heating, cooling, tightening, hydrating, brightening, and providing a glowing effect on the skin.

By allowing operators to swiftly connect and switch serum bottles, the device provides a tailored and personalized experience for patients. This customization ensures that diverse skin conditions can be treated effectively without the need to change large serum bottles attached to the console.

The multifunctional motor-driven handpiece's design offers operators flexibility in selecting specific skincare fluids based on individual patient needs. This adaptability enhances the device's efficacy in addressing a wide array of skin concerns.

The quick-connect serum bottle attachment prevents wastage of skincare fluids by enabling precise application. Operators can utilize the exact amount required for each treatment, minimizing unnecessary wastage and reducing overall operational costs.

The innovative design streamlines the treatment process, saving valuable time for both operators and patients. The quick-connect feature ensures rapid transitions between different skincare treatments, optimizing the workflow in professional skincare settings.

Current microdermabrasion techniques, including those that employ stationary abrasive tips or methods requiring manual movement for exfoliation, often necessitate multiple passes over the skin to achieve the desired level of exfoliation. These methods primarily focus on removing the outermost layer of the stratum corneum through linear or manual abrasive actions. However, these techniques can be inefficient and may lead to irritation due to the repetitive linear motion required to effectively abrade the skin surface.

The present invention introduces a motorized microdermabrasion tip that fundamentally enhances the exfoliation process through a unique combination of rotation and abrasion, offering a superior method for skin treatment. Unlike stationary tips, this motorized tip rotates at speeds ranging from 1 to 2000 revolutions per minute (rpm), allowing for a thorough, efficient, and less irritating exfoliation process. This innovation addresses and overcomes the limitations of current methods by:

1. Enhanced Exfoliation: The rotating abrasive tip engages the skin in a circular motion, which not only exfoliates the skin more deeply but also does so in a manner that is significantly less irritating to the patient. The circular motion allows for multiple layers of the skin to be treated in each pass, far exceeding the capabilities of stationary tips which require linear movement and are limited to surface-level exfoliation.

2. Stimulated Skin Regeneration: The rotation of the abrasive tip not only removes dead skin cells but also stimulates the underlying skin cells. This stimulation increases blood circulation, encouraging cellular renewal and resulting in healthier, more vibrant skin.

3. Integrated Cosmetic Fluid Infusion: A distinguishing feature of this invention is its ability to simultaneously infuse the skin with cosmetic fluids during the exfoliation process. This infusion aids in mitigating any potential trauma to the skin by ensuring it remains hydrated and nourished throughout the procedure, a feature not readily achievable with dry abrasion methods.

Technical Advantages Over Prior Art

This invention represents a significant leap forward in microdermabrasion technology. The motorized rotating tip offers a multi-faceted approach to skin treatment by combining deep exfoliation, enhanced skin stimulation, and simultaneous cosmetic fluid infusion. The ability to rotate at speeds up to 2000 rpm allows for precise control over the exfoliation intensity, tailoring the treatment to the specific needs of each patient while minimizing discomfort and irritation.

This capability is a clear departure from and improvement over existing stationary tip technologies, such as those utilized by hydrafacial systems, which are limited by their static nature and inability to deeply exfoliate or stimulate the skin in a circular motion.

According to the present invention, a device, i.e. a microdermabrasion device, for increasing the permeability of the skins surface to fluid and/or drug delivery is described. In general, permeation of drugs and/or fluids through the skin occurs at a slow rate, if at all. The stratum corneum acts as a barrier that limits the penetration of substances through the skin. Application of high-voltage pulses to the skin increases its permeability (electroporation) and enables the delivery of various substances into and through the skin. The application of electroporation to the skin has been shown to increase transdermal drug delivery. Moreover, electroporation, used alone or in combination with other enhancement methods, expands the range of drugs (small to macromolecules, lipophilic or hydrophilic, charged or neutral molecules) that can be delivered transdermally. The efficacy of transport depends on the electrical parameters and the physicochemical properties of drugs. The in vivo application of high-voltage pulses is well tolerated.

According to one embodiment of the invention, a device comprising an abrading surface, fluid delivery, current delivery; and fluid vaccuation is described. The device enhances fluid delivery through the stratum corneum by first delivering an abrasive media to the surface of the skin to prepare the skin for fluid delivery. Next, the device delivers fluid to the surface of the skin, with simultaneous current delivery (electroporation). The combination of skin abrasion, followed by simultaneous fluid delivery with electroporation allows for deep penetration of fluid through the skin by increasing the skin's permeability. In addition to enhancing fluid delivery through the stratum corneum, the device resurfaces the outer surface of the skin, removing dead skin cells and the outer layer of dermis, along with other superficial imperfections. Unlike known microdermabrasion devices, the results achieved with the device of the present invention will have enhanced and longer lasting results, namely, because skin enhancing fluids and drugs are delivered more deeply into the skin with the simultaneous electrooporation, and the electrical induced therapy itself has skin enhancing properties, such as increased collagen production, muscle tone, and overall skin elasticity and firmness.

The device and methods described herein have an efficient fluid supply/return for transdermal/topical delivery of skin enhancing drugs and medicaments. This feature of the invention has been found to be particularly important since presently known technologies use a gel which is applied to the skin which limits the penetration of effective ingredients because of the greater molecular weight of the gel. Macromolecule delivery through a liquid, which can be accomplished with the present invention, is accordingly more effective than prior art technologies which use a gel. The application of an abrasive as described in this invention solves this issue of lowering the impedence of the stratum corneum thus further improving drug delivery to the skin. Accordingly, the device and methods of the present invention, which include fluid delivery with electro-current and a vacuum source, enable simultaneous application of fluids containing skin enhancing drugs, with increased topical delivery through an abrading surface, to achieve the maximum effect. The abrading surface, which is applied to the skin preferably prior to fluid/drug delivery, increases topical drug delivery and penetration of the drug to the lower layers of the skin. These features of the invention are an improvement over prior art technologies which lack a fluid delivery and a vacuum source and more particularly in combination with an abrading surface and electro-current application to accomplish skin resurfacing and enhancement.

As used in this disclosure, the term "comprise" and variations of the term, such as "comprising" and "comprises," are not intended to exclude other additives, components, integers or steps.

In one embodiment, the present invention is a device for enhancing fluid delivery to the skin. The skin abrading device having fluid and current delivery is shown. The device comprises a handle, a tip, and a distal end. Positioned at the distal end are one or more conduits such as an electrical conduit, a fluid delivery conduit, and a vacuum conduit. The skin abrading device may further include one or more switches for controlling the device such as a switch and/or for controlling electrical current delivered via the electrical conduit, and/or control vacuum and/or fluid delivery from the fluid delivery and vacuum conduits. However, in other embodiments, these switches are positioned remotely on an adjunct device. The optional vacuum function of the evacuates fluid and skin debris from the surface of the skin and delivers the evacuated fluid and skin debris to an optional waste container (not shown) which may be positioned on the handle or in an adjunct device.

The handle may be cylindrical with molded hand grip, or it may have other configurations such as cylindrical (without a molded hand grip), or other variations, including elliptical, square, rectangular, and variations thereof. The handle may be formed of various materials as known to those in the art including any suitable plastic, metals, such as aluminum, stainless steel, and other alloys, and combinations of metal and plastic. Preferably, the handle is made from a high density plastic material.

The handle of the device comprises an interior and an outer casing. The fluid delivery conduit is positioned in the interior of the handle and delivers fluid from a reservoir (not shown) in an adjunct device through the fluid delivery conduit and out the tip of the device. The fluid exits the tip through a fluid delivery tip having one or more apertures. Also positioned within the interior of the handle is the vacuum conduit which pulls a vacuum from a vacuum pump stationed in an adjunct device through the vacuum conduit. The vacuum conduit has a vacuum entry port positioned within the tip for evacuating fluids and other debris from the surface of the skin. The interior of the device has one or more electrical conduits, which deliver current either to an electronics board, which then delivers current to one or more electrodes. Positioned within the tip is an abrading structure having an abrading end portion, which comprises an abrasive media. Within either the interior of the device, electronic control circuitry may be positioned for controlling current to the electrodes. In future iterations may include a portable device with miniature vacuum pump, supply and return reservoirs integrated as part of the handle without the need for an adjunct device as described.

The tip may be somewhat tapered at the end, or in other embodiments, the tip may be substantially cylindrically shaped or other, such as oval shaped, squared, or rectangularly shaped. The fluid delivery tip can be domed shaped, having a plurality of apertures, such that a spray effect is achieved with the fluid delivery tip. In other embodiments, the fluid delivery tip may be flat, and/or have a single aperture. Multiple apertures spread the liquid evenly along the area of the skin. Preferably, the fluid delivery tip is positioned with respect to the tip, electrodes, and abrading structure such that the fluid delivery tip extends slightly beyond or substantially flush with the abrading structure.

The tip of the dome creates a planar surface of the skin preventing the vacuum suction from causing a subcutaneous hemotoma which is caused when the lining of blood vessels are damaged and blood escapes through the skin.

The vacuum entry port is positioned with respect to the tip, such that the vacuum entry port minimizes skin trauma and ruptured capillaries, veins and arteries from the vacuum, yet creates a suitable vacuum to evacuate fluid and debris from the skin's surface. According to a preferred embodiment, the vacuum entry port is positioned on the tip such that when the tip of the device is applied to the surface of the skin, a space is created between the tip and the vacuum entry port to create a vacuum, known in the art as a closed loop system.

In a preferred embodiment, the fluid delivery tip is substantially flush to the skin with respect to the abrading end portion of the abrading structure and the electrodes such that when the device is applied to the skin, the skin stays relatively flat during treatment. According to this embodiment, when the abrasive media, vacuum, fluid, and electric current are applied to the skin with the configuration described with respect to this embodiment, having the various structures of the tip substantially flush to the skin minimizes the possibility of skin trauma associated with the pulling up of skin in a space of vacuum.

In an alternate embodiment, the vacuum entry port can be positioned in other portions of the tip to provide an optimal vacuum of concurrent liquid delivery and/or removal of skin debris. However, the vacuum entry port is preferably positioned to keep a higher level of fluid within the tip of the handle during treatment so as to have a higher absorption and penetration rate of ingredients contained in the fluid, into the skin, while still evacuating skin debris and preventing the fluid from flowing away from the desired treatment area and/or falling off the skin.

The abrading structure is positioned with respect to the tip, such that the abrading end portion of the abrading structure is substantially flush to the surface of the skin, in other embodiments, the abrading structure may be lowered or raised with respect to the end of the tip to provide skin contact, as desired by the user.

In a preferred embodiment, the abrading, structure has a range of abrasiveness on the abrasive media from a substantially smooth surface (no abrasion) to very abrasive depending on the treatment type. The abrading structure is positioned on the outer edge of both a fluid supply, i.e., the fluid delivery tip and vacuum port and on the inside of the electrodes. However, according to the present invention, other arrangements of the abrading structure, electrodes, and fluid delivery tip and vacuum port are possible, as will be understood by those of skill in the art.

The abrading structure may be reusable or disposable, in part or entirely. For example, according to one embodiment, the abrading end portion and the abrasive media are integral to the abrading structure. According to this embodiment, the abrading structure may be reusable or disposable in part or entirely. When the abrading structure is reusable, it is preferably designed to be sanitized and cleaned between uses and reused. In an alternate embodiment, the abrasive media is positioned on the abrading end portion in a removable fashion, such as a removable strip. According to this embodiment, the abrading structure is generally reusable and the abrasive media on the abrading end portion is preferably disposable.

The abrasive media comprises a material suitable to abrade the surface of the skin such as sand paper, rough textiles (such as dermal grade fabrics that are used in cosmetic microdermabrasion, typically made from 100% medical grade nylon and have a plurality of coatings and finishes), wire brushes, carbon fibers, and microneedles. The material can be conductive or non-conductive. According to one embodiment, the abrasive media comprises a non-conductive sand paper. In one embodiment, the sand paper is white aluminum oxide, a non-conductive material, readily available at low cost in medical grade. This material is able to withstand elevated temperatures, such as those typically present in any vitrification process that may be necessary for high volume binding/fabrication to produce the abrasive tip. According to other embodiments, a material softer than aluminum oxide is preferred so that the material is less irritating to the skin than aluminum oxide. According to this embodiment, the abrading media comprises polymeric beads. Generally, polymeric beads provide a softer, less irritating material than aluminum oxide. However, other materials according to the invention may be used as the abrading media, where the material is selected based on the particular individual to be treated and the purpose of the treatment. Accordingly, for different individuals, different materials may be substituted for the above-listed materials. In other embodiments, the abrasive media comprises a conductive material. Suitable conductive materials include, but are not limited to, metals, carbon, conductive polymers and conductive elastomers.

The abrading end portion may have a variety of suitable thicknesses and diameters. According to one embodiment, abrasive particles are coated onto the abrading end portion of the abrading structure. In some embodiments, the abrading structure and abrading end portion comprise a unitary plastic structure, such as acrylonitrile butadiene styrene (ABS). According to this embodiment, the abrasive media is an abrasive coating adhered to the abrading end portion, or the abrasive media is of a unitary construction with the abrading structure and abrading end portion. According to one embodiment, the abrasive media comprises abrasive particles which are adhered to the abrading end portion, where the thickness of the abrasive media is defined by the grit size of the abrasive particles. According to this embodiment, the abrasive particles are generally of a size ranging from about 300 to 50 grit (about 50 to 300 microns), and typically about 100 to 120 grit and may comprise carborundum (aluminum oxide), sodium bicarbonate, polymeric particles, and the like. Coarser particles (at the lower ends of the grit ranges (about 35 to 50, and typically less than 100) may also be provided for use in initial treatments, or treatments on coarser areas of the skin (such as arms), while finer particles (at the higher ends of the grit ranges about 300 and above) may be employed for subsequent treatments. Alternately, the abrading end portion may be formed by knurling, machining, laser treatment or otherwise mechanically or chemically treating the end of the abrading end portion to provide an integral abrasive media which has a unitary construction with the abrading end portion and abrading end structure. In a preferred embodiment, the abrasive media is abrasive particles having a grit size of about 120 or lower (approximately 0.0044 inches in diameter).

Typically the abrading end portion will have a thickness ranging from 0.5 microns to 150 microns, preferably ranging from 15 microns to 120 microns. The diameter of the abrading end portion is variable depending on the type of application. For example, in applications having a small area to be permeabilized, the abrading end portion can have a diameter of up to several micrometers, such as from 1 to 25 microns. For applications having a larger area to be permeabilized, the abrading end portion can have a diameter of up to several inches, such as from 0.1 to 5 inches (2.5 mm to 127 mm).

According to the present invention, a current (not shown) is delivered from the device to the surface of the skin through one or more electrodes. The electrodes can be a single electrode, or a plurality of nodes or combination thereof and may further have a variety of configurations and dimensions, such as nodes, bars, etc., as will be understood by those of skill the art.

Electrical currents, known for application to the skin, which may be used according to the present invention include:

a. Electroporation. Electroporation refers to the application of electric pulses to increase the permeability of cell membranes. According to the present invention, electric pulses are applied to skin cells to increase membrane permeability.

b. Microcurrent. Microcurrent refers to the application of a small current used in a noninvasive electrotherapy technique where electrodes are applied at acupuncture points. In general, 10-500 microamps (Ua) are applied to the surface of the skin and for optimal effectiveness, the current applied to the skin should not cause an actual "visual" contraction of the facial muscles. In some applications, electroporation refers to the process of applying a microcurrent to the surface of the skin.

c. Iontophoresis. Iontophoresis refers to a therapeutic type of transcutaneous drug delivery in which electric current is applied to the skin to enhance absorption of large polar or hydrophilic molecules and peptides—e.g., insulin, and control therapeutic delivery. According to the present invention, a galvanic current is applied an ionizable agent in contact with a surface of the skin, by means of an appropriate electrode, to hasten the movement into the tissue of the ion of opposite charge to that of the electrode. Accordingly, skin enhancing agents which are polar or hydrophilic may be delivered into the skin.

d. Sonophoresis. Sonophoresis refers to a process that exponentially increases the absorption of semisolid topical compounds (transdermal delivery) into the epidermis, dermis and skin appendages. Sonophoresis occurs where ultrasound waves stimulate micro-vibrations within the skin epidermis and increase the overall kinetic energy of molecules making up topical agents. Skin enhancing agents may be mixed with a coupling agent (gel, cream, ointment) to transfer ultrasonic energy from the ultrasound transducer (i.e., electrode) to the skin and enhancing drug transport through the skin.

e. Galvanic. Galvanic or Galvanic current refers to the current which is the electrical current used in the process of Iontophoresis.

f. Ultrasound. Ultrasound or ultrasonic current refers to the current used in Sonophoresis. Ultrasound is cyclic sound pressure with a frequency greater than the upper limit of human hearing. Although this limit varies from person to person, it is approximately 20 kilohertz (20,000 hertz) in healthy, young adults and thus, 20 KHz serves as a useful lower limit in describing the ultrasonic current applied via the electrodes in the present invention.

g. Ultrasonic Cavitation. Ultrasonic Cavitation refers to an advanced ultrasonic machine having 3 MHz and 1 MHz ultrasound frequencies for the body and a 1.4 MHz ultrasonic frequency for the face, and an ultrasonic cavitation wavelength at 47 KHz. In Ultrasonic Cavitation, the ultrasonic waves are able to act on the skin surface (3 MHZ ultrasound), providing skin tightening as well in the deep layers, (cavitation) providing real results, after the treatment, in terms of cellulite and localized adiposity. It has been shown to be able to eliminate centimetres of belly, buttocks, hips and thighs without any side effects. Ultrasonic waves in a specific range from 20 to 70 KHz are able to cause the "cavitation" effect: focused high energy waves which creates micro bubbles of vapor inside the adiposities and in the interstitial liquids of cellulite.

h. Acoustic cavitation. Acoustic Cavitation refers to a non-flowing system where the ambient pressure can be varied by sending sound waves through a liquid. The ultrasonic sound waves are made up of alternate compressions and rarefactions. During the rarefaction cycle (low pressure) a lot of microscopic bubbles will grow and during the compression cycle (high pressure) each bubbles undergoes a collapse or implosion.

i. Mesotherapy. Mesotherapy refers to a procedure in which multiple tiny injections of pharmaceuticals, vitamins, etc., are delivered into the mesodermal layer of tissue under the skin, to promote the loss of fat or cellulite.

J. Radio Frequency. Refers to a procedure using a beam of radio frequency energy to target deeper layers of the skin by heating them up. This creates stimulation of the skin and in particular, the collagen, a substance which gives elasticity to the skin. The radio frequencies cause water molecules in the deeper layers of skin to vibrate. This in turn creates friction which causes the heating effect. When heat is applied to collagen fibres, they shrink and tighten up, and over time following the treatment, new collagen also forms.

k. Not and cold therapies. Refers to using an electrical current and other modalities to create different adjustable temperatures ranging from hot (up to 140 degrees Fahrenheit) to cold (down to 5 degrees Fahrenheit) to treat the surface layer skin by softening and/or tightening collagen fibers.

In a preferred embodiment of the present invention, a microcurrent is applied to the skin, i.e., electroporation. According to this embodiment, the current of the device is set for a wave form with power between 10-500 microamps (Ua). The current is delivered through the device 100 and through one or more electrodes to the surface of the skin. Treatment can be substantially stationary in certain areas, or vary in the degree of motion, up to sweeping lines.

According to another embodiment, a combination of two or more frequencies of current are applied from the device to a patient. Accordingly, in some embodiments the device is capable of delivering a plurality of different frequencies (i.e., types) of current, either individual applied or concurrent. For example, an ultrasonic current may be applied from the device to a patient, followed by delivery of a microcurrent from the device to the same patient. The treatment may be in one treatment area, or over a plurality of treatment areas, such the delivery of microcurrent to the face, followed by delivery of ultrasonic current to the arms. The plurality of frequencies may be used on one patient for application of different electric currents. For example, ultrasound and microcurrent have different ways of penetrating fluids and treating the skin. The concurrent combination of these and other electric modalities shown in device is to provide a more effective treatment.

Fluid is delivered from a fluid reservoir (not shown), which may be either part of the handle or in a separate reservoir, such as a plastic or glass tube serum, through the fluid delivery conduit and out the fluid delivery tip in the tip of the device. Fluid delivery may be used in the device for cleaning of the skin, as a vehicle for delivery of a therapeutic agent, or it may be the therapeutic agent itself, and/or the fluid may be an ionic agent to facilitate delivery of current through the electrodes. The fluid may include one or a plurality of suitable skin enhancing agents, and/or conductive ingredients, or other suitable agents for skin cleaning and skin enhancement or facilitation of current delivery, such as water, salts, ionic or non-ionic surfactants, preservatives, alcohol, glycerol, gel, and other similar agents. Various mixtures of these agents may be formulated into fluids with various conductivity levels, depending on the desired application. Preferably, at least one of the fluids used in a method according to the present invention is a "highly conductive fluid" or a "fluid with a high conductivity" meaning a fluid with a conductivity from about 1,000 to about 100,000 (μSiemens/cm) to facilitate current delivery. Other fluids, such as a "fluid with a low conductivity", meaning a fluid with a conductivity from about 0.1 to about 999 (μSiemens/cm), are used according to the invention in other applications, such as cleaning, and/or delivery of a skin enhancing or therapeutic agent. A highly conductive fluid is used according to the present invention to provide a conductive path through the skin, in a preferred embodiment, at least one fluid with a conductivity of at least 500 to about 50,000 μSiemens/em is used.

Therapeutic or skin enhancing fluids useful in the device according to the present invention may be of a variety of therapeutic agents. For example, the fluid may be a skin treatment liquid, a lotion liquid, and/or a vitamin liquid, or a combination thereof. The fluid may also be a pharmacologically-active agent, where the fluid carries a chemical agent of a suitable concentration. Examples of such agents include TCA (trichioroacetic acid), a glycolic acid including an alphahydroxy acid (AHA), a lactic acid, a citric acid, and phenol, alone or in combination with other agents or fluids. Examples of other therapeutic or skin enhancing agents include type A botulinum toxine, phosphatidylcoline, aminophylline, hyaluronic acid, L-carnitine, vitamins, amino acids, collagen, lidocaine, heparin, elastine, compounds for Mesotherapy procedures, glutathione, hormone replacement agents, hyaluronidase, MTE-4 (Copper-Manganese-Zinc Sulphate-Chromium), ionic skin tissue growth gels, enzymes, peptides and steroids.

Other ingredients can include plant and fruit derived ingredients, such as enzymes and stem cells derived from fruits and/or plants, etc. Since microdermabrasion is a controlled injury of the skin by abrading the surface layer to cause a wound healing response, other known healing and anti-inflammatory ingredients such as cortisone, aloe extract, etc. may be used to increase healing response time and also act as an anti-fungal, anti-viral, anti-bacterial and acaricidal activity against skin infections such as acne, etc, may be used individually or in any combination with other sterile fluids, drugs, and other skin enhancing and/or therapeutic agents.

Other agents and preferred viscosity parameters may be found in "Advanced drug delivery reviews", 56 (2004) 659-674, A vacuum may be applied to the surface of the skin from a vacuum pump (not shown) through the vacuum conduit and vacuum entry port on the tip of the device. Preferably, the vacuum pump which supplies the vacuum to the device has a rating of 2.9 A, with a max flow rate of 2 cu.ft/min, a power rating of 120 W, with a 60 Hz frequency, and preferably RoHS compliant, although other embodiments are possible. In general, the vacuum, used during a treatment and applied to the surface (or just above) the skin of a patient, is a continuous flow and preferably can be adjusted with a flow control valve to increase or decrease vacuum pressure.

A skin abrading device, having a plurality of removable, exchangeable, and attachable tips, according to a preferred embodiment of the invention is shown. The tip of the device comprises multiple nesting (e.g., interconnected) structures which are removable/attachable from the handle. The outer structure of the tip comprises the electrodes at the proximal end of the tip and wiring for delivering current to the electrodes. Positioned within the outer structure, is the intermediate structure, which is also the abrading structure. The inner structure comprises the fluid delivery tip and vacuum entry port.

The inner structure is located at the center of the tip. The outer structure is located at the periphery of the tip. The intermediate structure is located between the inner structure and the outer structure. The outer structure, intermediate structure, and the inner structure are coaxial with each other and are in a ring shape. Preferably, the outer structure and intermediate structure form an outer ring and intermediate ring respectively at the tip. The outer ring and intermediate ring can be formed in a circular shape or a non-circular shape. Therefore, the abrading end portion forms at the intermediate ring and encircles the fluid delivery tip and vacuum entry port of the fluid delivery. The electrodes are aligned at the outer ring to encircle the abrading end portion at the intermediate ring.

The outer structure, intermediate structure and inner structure are connected to the handle with a suitable connection, such as compression fitting, threaded fittings, etc. In a preferred embodiment, one or more of the outer structure, intermediate structure, and inner structure comprise stainless steel. In one preferred embodiment, the intermediate structure comprises a reusable stainless steel abrading structure having an abrading end portion which has a diamond coated abrasive as the abrasive media. In another preferred embodiment, the intermediate structure comprises a disposable (preferably translucent) plastic abrading structure having a disposable abrasive media positioned on the abrading end portion. In another preferred embodiment, the inner structure, comprising the fluid delivery tip and the vacuum entry port, are one or more of transparent, detachable, and/or disposable. Although the outer structure, intermediate structure, and inner structure have been described herein as removable, exchangeable, and attachable, it will be understood by those of skill in the art that one or more of the outer structure, intermediate structure, and inner structure may be affixed to the handle in a permanent, or not-easily removable fashion. However, in other embodiments, one or all of the structures may be one piece in any arrangement or separate individual connections. For example, the device may comprise a handle with an electric current node (i.e., electrode) in the middle surrounded by a fluid delivery piece and an abrasive structure making the outer edge of the handle. This is just an opposite arrangement, and as it will be understood by those of skill in the art, interrelationship of the various tips shown in the Figures is by way of example and other configurations are within the scope of the invention.

In another embodiment of the abrading structure, abrading end portion of the abrading structure comprises one or more grooves. The grooves may be differently shaped, such as rounded grooves, or slotted squares. The grooves are provided to abrade the skin more effectively by stretching it, and to better guide skin debris into the vacuum. Preferably, to keep the vacuum sealed, the grooves are substantially even with the edge such that when the abrading structure is applied to the skin, air does not escape. The grooves may have a variety of thickness or radius, shape or design, for different skin types and applications, as will be understood by those of skill in the art. According to this embodiment, extraction can be realized by pressing the abrading end portion and grooves to the skin, such that the grooves act as an extractor on a pore. For example, when the abrading end portion having grooves is pressed to the skin, oil and sebum will be released from the pores.

Other embodiments of the present invention are methods, including the following:

A method for skin exfoliation and serum infusion, comprising:

Positioning a motorized exfoliating tip onto a targeted treatment area of the skin;

Activating the motorized exfoliating tip to perform circular, oscillatory, or multidirectional motion over the stationary treatment spot;

Simultaneously infusing a treatment serum through a fluid conduit integrated within or external to the motorized tip;

Applying vacuum suction to remove exfoliated debris and enhance serum penetration without requiring manual movement across the skin.

The exfoliation and infusion may occur simultaneously, allowing deeper serum penetration into the freshly abraded skin layers;

The motorized tip operates between 10-2000 RPM, eliminating the need for manual force or repetitive passes.

A method for spot-treatment microdermabrasion, comprising:

Placing the motorized exfoliation tip directly on a target skin spot without requiring linear movement of the hand;

Engaging the motorized exfoliation mechanism to abrade the skin and deliver serum in a localized area;

Utilizing a vacuum-assisted debris removal system to clear exfoliated skin without clogging pores or requiring manual wiping;

Allowing the skin treatment to be applied precisely and efficiently without excessive manual pressure or motion.

A method for automated exfoliation and fluid infusion without manual pressure, comprising:

Activating a motorized, vacuum-assisted exfoliation system;

Placing the motorized tip on the skin without requiring force to initiate exfoliation;

Delivering serum into the skin at the moment of exfoliation, ensuring higher fluid absorption than static tips;

Controlling the exfoliation speed and depth electronically, rather than relying on manual hand pressure.

A method for increasing serum penetration beyond the stratum corneum, comprising:

Exfoliating a targeted skin area using a motorized tip that moves in a controlled circular motion;

Applying negative vacuum pressure to simultaneously lift and open microchannels in the exfoliated skin;

Infusing a treatment solution through the exfoliating tip, ensuring serum delivery reaches deeper skin layers;

Maintaining constant contact with the skin without requiring linear manual passes or repetitive movements.

A method for reducing operator fatigue in microdermabrasion treatments, comprising:

Using a motorized exfoliation device that performs automatic spot treatment;

Eliminating the need for manual scraping, pressure application, or repetitive linear strokes;

Allowing the vacuum-assisted debris removal to work in tandem with motorized exfoliation, ensuring a clean and efficient procedure;

Enhancing treatment precision by stabilizing the device on the skin, rather than relying on manual control of abrasion intensity.

A method for preventing cross-contamination in professional skin treatments, comprising:

Using a disposable motorized exfoliation tip with pre-applied abrasive coating;

Ensuring each treatment is conducted with a fresh tip, reducing the risk of bacterial transmission;

Integrating a fluid delivery system that directly infuses serum, preventing the need for manual serum application post-exfoliation;

Combining exfoliation, infusion, and vacuum-assisted removal into a single-use, contamination-free treatment cycle.

A method for dynamic skin resurfacing with adjustable exfoliation speed, comprising:

Providing a motorized exfoliation tip with variable speed settings;

Allowing real-time speed adjustments to cater to different skin types and conditions;

Using a sensor-controlled system to automatically adjust exfoliation speed based on skin resistance;

Delivering customized skin treatment without requiring manual speed adjustments by the operator.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense. Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed.

What is claimed is:

1. A microdermabrasion device with a serum bottle attached, comprising:

a tip comprising multiple nesting structures being an outer structure of the tip comprising electrodes at the proximal end of the tip and wiring for delivering current to the electrodes, an intermediate structure positioned within the outer structure and an inner structure comprises a fluid delivery tip and vacuum entry port;

wherein the inner structure is located at the center of the tip, the outer structure is located at the periphery of the tip and the intermediate structure is located between the inner structure and the outer structure;

wherein the outer structure, intermediate structure, and the inner structure are coaxial with each other and are in a ring shape;

wherein the intermediate structure encircles the fluid delivery tip and vacuum entry port of the fluid delivery; and wherein electrodes are aligned at the outer structure to encircle an abrading end portion of the intermediate structure;

one or more fluid apertures positioned on the inner structure to facilitate both vacuum suction and fluid outlet functionalities; and one or more grooves, wherein:

wherein the grooves are structured to guide exfoliated debris toward the vacuum port and enhance fluid flow the tips are crafted from a plastic material; and the tips have an abrasive coating affixed via an adhesive-based bonding process;

a quick-connect serum bottle attachment attached at a downward-sloping incline to the microdermabrasion device, comprising a housing for serum, a serum cartridge, a coupling part for the serum cartridge, wherein the housing envelops the serum cartridge to hold it in place on a superior aspect of the microdermabrasion device and the coupling part has a notch configured to receive and retain a protrusion on the serum cartridge; and an opening molded to mate with a serum bottle, wherein:

the opening comprises a male connection equipped with threads or a puncturing tube;

the serum bottle is fitted with a cap or foil cap, threaded or connected to the male tube upon insertion; and the male tube punctures or threads onto the serum bottle, forming a secure seal and allowing fluid to flow through a vacuum tube inside a handpiece, wherein serum flows through the spindle shaft and the attached multifunctional tip onto the skin applying surface;

a first tubing segment connected to the opening, wherein the first tubing segment is in a kidney bean shape configured to hold serum;

a second tubing segment connecting the first tubing segment to a first tube coupling attached to the core inlet rearward of a motor, wherein the second tubing segment travels around the motor from the first tubing segment to the first tube coupling;

wherein the quick-connect serum bottle attachment attached at a downward-sloping incline to the microdermabrasion device is mounted forward of the motor, the motor powering the tip.

2. The tip for a microdermabrasion device of claim 1, wherein the abrasive coating is Emery sand.

3. The tip for a microdermabrasion device of claim 2, further comprising an Epoxy resin adhesive.

4. The tip for a microdermabrasion device of claim 3, wherein the adhesive is electrostatically sprayed onto the surface and then the sand is electrostatically sprayed onto the surface.

5. The tip for a microdermabrasion device of claim 4, wherein tip is baked at a temperature of 80° C. for 2 hours.

6. A method for skin exfoliation and serum infusion using the device of claim 1, comprising:

Positioning the motorized exfoliating tip onto a targeted treatment area of the skin;

Activating the motorized exfoliating tip to perform circular, oscillatory, or multidirectional motion over the stationary treatment spot;

Simultaneously infusing a treatment serum through a fluid conduit integrated within or external to the motorized tip; and Applying vacuum suction to remove exfoliated debris and enhance serum penetration without requiring manual movement across the skin.

7. The method of claim 6, wherein:

the exfoliation and infusion occur simultaneously, allowing deeper serum penetration into the freshly exfoliated skin layers; and the motorized tip operates between 10-2000 RPM, eliminating the need for manual force or repetitive passes.

8. A method for spot-treatment microdermabrasion using the device of claim 1, comprising:

Placing the motorized exfoliation tip directly on a target skin spot without requiring linear movement of the hand;

Engaging the motorized exfoliation mechanism to abrade the skin and deliver serum in a localized area;

Utilizing a vacuum-assisted debris removal system to clear exfoliated skin without clogging pores or requiring manual wiping; and Allowing the skin treatment to be applied precisely and efficiently without excessive manual pressure or motion.

9. The method of claim 8, further comprising:

Activating the motorized, vacuum-assisted exfoliation system;

Placing the motorized tip on the skin without requiring force to initiate exfoliation;

Delivering serum into the skin at the moment of exfoliation, ensuring higher fluid absorption than static tips; and Controlling the exfoliation speed and depth electronically, rather than relying on manual hand pressure.

10. The method of claim 8, further comprising:

Exfoliating a targeted skin area using the motorized tip that moves in a controlled circular motion;

Applying negative vacuum pressure to simultaneously lift and open microchannels in the exfoliated skin;

Infusing a treatment solution from the serum cartridge through the motorized tip, ensuring treatment solution delivery reaches deeper skin layers; and Maintaining constant contact with the skin without requiring linear manual passes or repetitive movements, wherein treatment solution penetrates beyond the stratum corneum.

11. The method of claim 8, further comprising:

Using the motorized exfoliation tip to perform automatic spot treatment;

Eliminating the need for manual scraping, pressure application, or repetitive linear strokes;

Allowing the vacuum-assisted debris removal to work in tandem with motorized exfoliation, ensuring a clean and efficient procedure; and Enhancing treatment precision by stabilizing the device on the skin, rather than relying on manual control of abrasion intensity.

12. The method of claim 8, further comprising:

Using a disposable motorized exfoliation tip with pre-applied abrasive coating;

Ensuring each treatment is conducted with a fresh tip, reducing the risk of bacterial transmission;

Integrating a fluid delivery system that directly infuses serum, preventing the need for manual serum application post-exfoliation; and Combining exfoliation, infusion, and vacuum-assisted removal into a single-use, contamination-free treatment cycle.

13. The method of claim 8, further comprising:

Providing the motorized exfoliation tip with variable speed settings;

Allowing real-time speed adjustments to cater to different skin types and conditions;

Using a sensor-controlled system to automatically adjust exfoliation speed based on skin resistance; and Delivering customized skin treatment without requiring manual speed adjustments by the operator.

* * * * *